United States Patent
Kitagawa et al.

(10) Patent No.: US 9,603,714 B2
(45) Date of Patent: Mar. 28, 2017

(54) SPACER AND EXPANDING DEVICE

(71) Applicant: TERUMO KABUSHIKI KAISHA, Shibuya-ku (JP)

(72) Inventors: Tomomi Kitagawa, Fujinomiya (JP); Yasuyuki Honma, Ashigarakami-gun (JP)

(73) Assignee: TERUMO KABUSHIKI KAISHA, Shibuya-ku, Tokyo (JP)

( * ) Notice: Subject to any disclaimer, the term of this patent is extended or adjusted under 35 U.S.C. 154(b) by 507 days.

(21) Appl. No.: 14/030,113

(22) Filed: Sep. 18, 2013

(65) Prior Publication Data

US 2014/0094920 A1 Apr. 3, 2014

(30) Foreign Application Priority Data

Sep. 28, 2012 (JP) ................................. 2012-215524

(51) Int. Cl.
*A61F 2/44* (2006.01)
*A61B 17/70* (2006.01)
*A61B 17/00* (2006.01)

(52) U.S. Cl.
CPC .......... *A61F 2/442* (2013.01); *A61B 17/7065* (2013.01); *A61B 2017/00557* (2013.01)

(58) Field of Classification Search
CPC .... A61F 2/4405; A61F 2/441; A61B 17/7065; A61B 17/7062; A61B 17/7067; A61B 17/7097
See application file for complete search history.

(56) References Cited

U.S. PATENT DOCUMENTS

| | | | |
|---|---|---|---|
| 2007/0173940 A1* | 7/2007 | Hestad ...................... | A61F 2/44 623/17.12 |
| 2007/0270823 A1 | 11/2007 | Trieu et al. | |
| 2009/0118833 A1 | 5/2009 | Hudgins et al. | |
| 2009/0299373 A1 | 12/2009 | Sisken | |
| 2011/0082504 A1* | 4/2011 | Singhatat ........... | A61B 17/7065 606/249 |
| 2011/0137317 A1 | 6/2011 | O'Halloran et al. | |

OTHER PUBLICATIONS

Extended Search Report issued on Nov. 27, 2013 by the European Patent Office, in corresponding European Patent Application No. 13185551.2. (6 pages).

* cited by examiner

*Primary Examiner* — Eduardo C Robert
*Assistant Examiner* — Julianna N Harvey
(74) *Attorney, Agent, or Firm* — Buchanan Ingersoll & Rooney PC

(57) ABSTRACT

An expanding device for expanding the spacing between bones is provided. The expanding device includes a spacer configured to be expandable and disposed between the bones, a catheter provided with the spacer at a distal end thereof and adapted to introduce a filler into the spacer, and a sheath having a lumen through which the catheter is inserted and in which the spacer before expansion can be housed. The spacer includes a spacer body configured to be expandable, an introduction section through which a filler is introduced into a rear-end-side expansion section of the spacer body, and a bypass passage through which part of the filler in the introduction section is introduced into a distal-end-side expansion section of the spacer body.

12 Claims, 19 Drawing Sheets

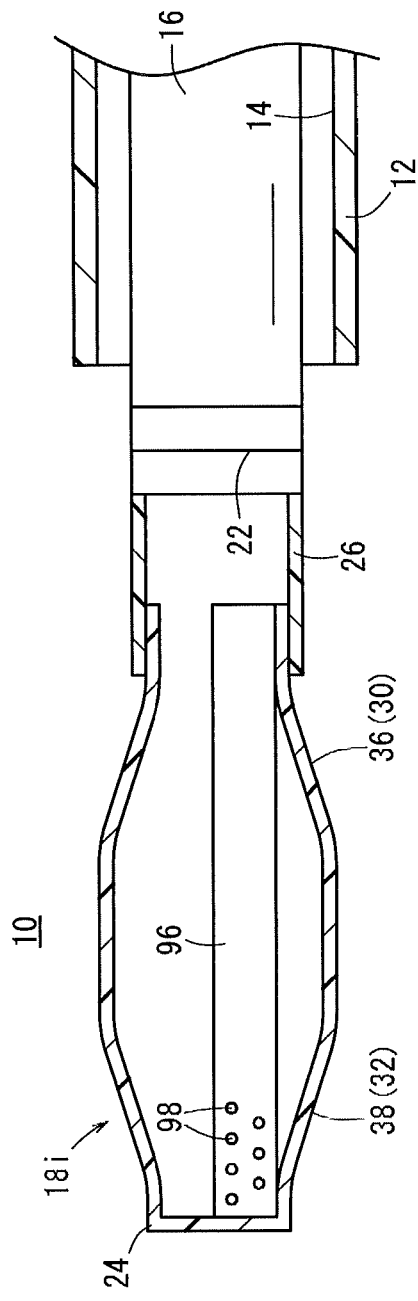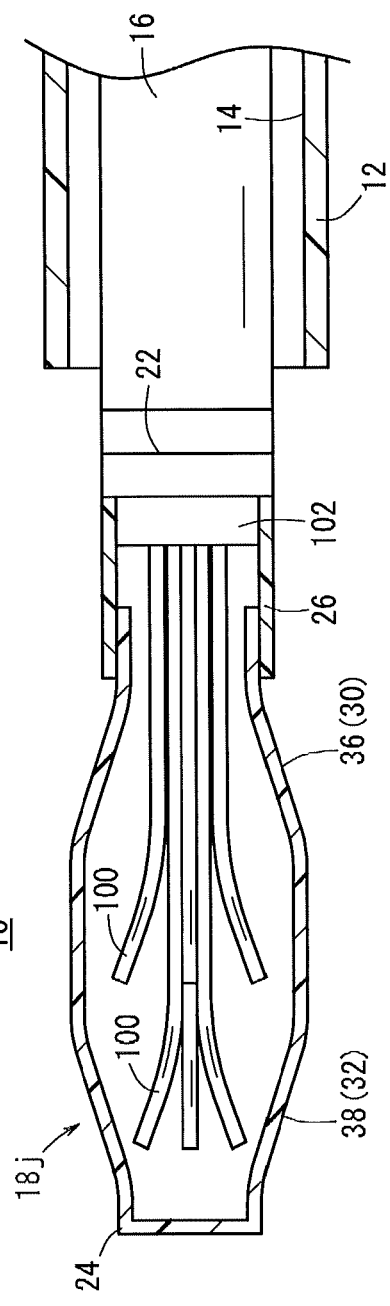

SPACER AND EXPANDING DEVICE

CROSS-REFERENCE TO RELATED APPLICATION

This application is based upon and claims the benefit of priority from Japanese Patent Application No. 2012-215524 filed on Sep. 28, 2012, the contents of which are incorporated herein by reference.

BACKGROUND OF THE INVENTION

Field of the Invention

The present invention relates to a spacer and an expanding device for expanding the spacing between bones.

Description of the Related Art

Lumbar spinal canal stenosis is a disease in which the spinal canal is stenosed due to regressive degeneration of an intervertebral disc, ligament or the like, and which would cause such a symptom as lumbar pain, leg pain, or intermittent claudication. Treatment of the lumbar spinal canal stenosis is mainly carried out by an operation of resecting the vertebra in the part where the spinal canal is narrowed (laminectomy) or an operation of fixing the vertebra (spondylodesis). On the other hand, as a technique that is less invasive as compared with the laminectomy and spondylodesis, a method has been developed in recent years in which a metallic spacer is set indwelling in an interspinal area (between spinous processes) so as to remove a pressure on the spinal nerve or nerve root. This method, however, needs incision of muscles and ligament in the back in order to set the spacer indwelling in a desired area, so that the patient has to undergo such an invasive procedure and be kept hospitalized for a long period of time.

In order to solve these problems, another method has been proposed in which a spacer is inserted into an interspinal area in a less-invasive manner, to be left indwelling there. In this another method, first, a sheath is percutaneously inserted into the interspinal area. Then, an expandable spacer provided in a folded state at a distal end of a catheter is inserted and passed in the lumen of the sheath, to be disposed in the interspinal area. Thereafter, a filler such as bone cement is loaded into the spacer to expand the spacer, and the spacer is left indwelling in the interspinal area, or between spinous processes (see, for example, U.S. Patent Application Publication No. 2009/0118833). The filler is hardened after the spacer has been filled with the filler, so that the expanded state of the spacer can be maintained semi-permanently.

SUMMARY OF THE INVENTION

In the case of setting a spacer indwelling in an interspinal area, the center of the spacer in the axial direction has to be positioned at the center in the width direction of the interspinal ligament between adjacent spinous processes. When the spacer disposed between the spinous processes is filled with a filler, however, the spacer may be displaced (may slip) with respect to the spinous processes, whereby the center of the spacer in the axial direction may be shifted from the center of the interspinal ligament in the width direction.

This arises from precedent expansion of either one of a distal-end-side portion and a rear-end-side portion of the spacer, which is caused by asymmetrically folding of the spacer in the axial direction or by contact of the spacer with the surrounding tissue (bone, muscle, ligament or the like).

More specifically, for example in the case where the distal-end-side portion of the spacer is expanded in advance of the rear-end-side portion, the distal-end-side portion of the spacer makes contact with the spinous processes, with the rear-end-side portion of the spacer not in contact with the spinous processes. In this situation, a reaction force tending to push the spacer toward the distal-end side is exerted on the spacer from the spinous processes. This would result in a displacement of the spacer relative to the spinous processes toward the distal-end side.

Similarly, for example in the case where the rear-end-side portion of the spacer is expanded in advance of the distal-end-side portion, the rear-end-side portion of the spacer makes contact with the spinous processes, with the distal-end-side portion of the spacer not in contact with the spinous processes. In this instance, a reaction force tending to push the spacer toward the rear-end side is applied to the spacer from the spinous processes. Consequently, the spacer would be displaced toward the rear-end side relative to the spinous processes.

Such a displacement as above-mentioned becomes more conspicuous in the case where the spacer has a largely recessed and projected shape, such as a so-called H-type shape or dumbbell-type shape. When the center of the spacer in the axial direction is largely deviated from the center of the interspinal ligament in the width direction due to the displacement, the spacer may be detached from the interspinal area.

The present invention has been made in view of the above problems, and an object of the present invention is to provide a spacer and an expanding device by which it is ensured that at the time of filling the spacer with a filler, displacement of the spacer can be restrained or prevented and the spacing between bones can thereby be expanded reliably.

[1] According to one aspect of the present invention, there is provided a spacer which is set indwelling between bones and for expanding the spacing between the bones, the spacer including a spacer body configured to be expandable, an introduction section through which a filler is introduced into a rear-end-side expansion section of the spacer body, and a bypass passage through which part of the filler in the introduction section is introduced into a distal-end-side expansion section of the spacer body.

With the spacer according to the present invention, it is possible to introduce the filler into the rear-end-side expansion section of the spacer body through the introduction section, and to introduce part of the filler in the introduction section into the distal-end-side expansion section of the spacer body through the bypass passage. Therefore, the distal-end-side portion and the rear-end-side portion of the spacer body can be expanded substantially simultaneously. In other words, it is possible to prevent either one of the distal-end-side portion and the rear-end-side portion of the spacer body from expanding in advance of the other. Therefore, displacement of the spacer body (spacer) can be restrained. Consequently, the spacing between bones can be expanded reliably.

[2] In the above-mentioned spacer, a configuration may be adopted in which the introduction section and the bypass passage are so formed that the introduction of the filler into the rear-end-side expansion section through the introduction section and the introduction of the filler into the distal-end-side expansion section through the bypass passage are started substantially simultaneously, and that the quantity of the filler introduced into the rear-end-side expansion section through the introduction section per unit time and the quantity of the filler introduced into the distal-end-side expansion section through the bypass passage per unit time are substantially the same.

With the above configuration, the introduction of the filler into the rear-end-side expansion section of the spacer body through the introduction section and the introduction of the filler into the distal-end-side expansion section of the spacer body through the bypass passage are started substantially simultaneously. Further, the quantity of the filler introduced into the rear-end-side expansion section through the introduction section per unit time and the quantity of the filler introduced into the distal-end-side expansion section through the bypass passage per unit time are substantially the same. Thus, the distal-end-side portion and the rear-end-side portion of the spacer body can be expanded substantially simultaneously and substantially symmetrically. Therefore, displacement of the spacer can be preferably prevented.

[3] In the above-mentioned spacer, a configuration may be adopted in which the introduction section is connected to a rear end portion of the spacer body, and an outlet for the filler of the bypass passage is located at a distal end portion of the spacer body.

With this configuration, the introduction section is connected to a rear end portion of the spacer body, and the outlet for the filler of the bypass passage is located at a distal end portion of the spacer body. Therefore, the filler can be reliably introduced into the rear-end-side expansion section through the introduction section, and the filler can be reliably introduced into the distal-end-side expansion section through the bypass passage.

[4] In the above-mentioned spacer, the bypass passage may be disposed inside the spacer body.

With this configuration, the bypass passage is disposed inside the spacer body, so that an increase in the size of the spacer can be suppressed as compared with the case where the bypass passage is disposed outside the spacer body.

[5] In the above-mentioned spacer, the bypass passage may be fixed to an inner surface of the spacer body.

With this configuration, the bypass passage is fixed to an inner surface of the spacer body, so that displacement of the bypass passage inside the spacer body at the time of introducing the filler into the spacer body can be prevented. Consequently, the filler can be reliably introduced into the distal-end-side expansion section of the spacer body through the bypass passage.

[6] In the above-mentioned spacer, the bypass passage may be fixed to at least one of a distal end portion and a rear end portion of the spacer body.

With this configuration, the bypass passage is fixed to at least either one of the distal end portion and the rear end portion of the spacer body which are comparatively less deformed at the time of expansion of the spacer body. Therefore, a situation in which the bypass passage is detached from the spacer body during introduction of the filler into the spacer body can be suitably avoided.

[7] In the above-mentioned spacer, a configuration may be adopted in which the bypass passage is flexible, and a portion of the bypass passage that is located inside the spacer body is secured to an inner surface of the spacer body over substantially the whole length of the portion.

With this configuration, the portion of the bypass passage that is located inside the spacer body is secured to the inner surface of the spacer body over substantially the whole length of the portion. Therefore, the area of contact (the area of securing, or the area of adhesion) between the bypass passage and the spacer body can be easily enlarged. This makes it possible to secure the bypass passage to the spacer body more firmly and, therefore, to suitably avoid a situation in which the bypass passage is detached from the spacer body during introduction of the filler into the spacer body. In addition, since the bypass passage is flexible, it is ensured that upon expansion of the spacer body, the shape of the bypass passage can be deformed along the shape of the expanded spacer body. Consequently, the expansion of the spacer body can be effectively prevented from being hampered by the bypass passage.

[8] In the above-mentioned spacer, a configuration may be adopted in which the introduction section extends to the rear-end-side expansion section in the spacer body, and an outlet for the filler of the bypass passage is located at the distal-end-side expansion section.

With this configuration, the introduction section extends to the rear-end-side expansion section in the spacer body, and the outlet for the filler of the bypass passage is located at the distal-end-side expansion section. Therefore, it is possible to reliably introduce the filler into the rear-end-side expansion section through the introduction section. Further, it is possible to reliably introduce the filler into the distal-end-side expansion section through the outlet of the bypass passage.

[9] In the above-mentioned spacer, the bypass passage may be flexible and be fixed to an outer surface of the spacer body in the state of being disposed outside of the spacer body.

With this configuration, the bypass passage is disposed outside the spacer body, so that the configuration of the spacer can be simplified as compared with the case where the bypass passage is disposed inside the spacer body. In addition, the bypass passage is fixed to the outer surface of the spacer body, so that the bypass passage can be prevented from being caught on tissues around the spacer body. Furthermore, since the bypass passage is flexible, the expansion of the spacer body can be effectively prevented from being obstructed by the bypass passage.

[10] According to another aspect of the present invention, there is provided an expanding device for expanding a spacing between bones, including a spacer configured to be expandable and disposed between the bones, a catheter provided with the spacer at a distal end thereof and adapted to introduce a filler into the spacer, and a sheath having a lumen through which the catheter is inserted and in which the spacer before expansion can be housed, wherein the spacer is any of the above-mentioned spacers.

With the expanding device of the other aspect of the present invention, the same effects as those of the above-mentioned spacers are obtained.

With the spacer and the expanding device according to the present invention, the filler can be introduced into the rear-end-side expansion section of the spacer body through the introduction section, and part of the filler in the introduction section can be introduced into the distal-end-side expansion section of the spacer body through the bypass passage. Therefore, displacement of the spacer at the time of loading the spacer with the filler can be prevented. Consequently, the spacing between bones can be expanded reliably.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 19A is a partly-omitted schematic enlarged sectional view of an expanding device including a spacer according to a ninth modification of the present invention, and FIG. 19B is a partly-omitted schematic enlarged sectional view of an expanding device including a spacer according to a tenth modification of the present invention.

DESCRIPTION OF THE PREFERRED EMBODIMENTS

Now, a spacer and an expanding device including the spacer according to the present invention will be described below, by showing preferred embodiments thereof and while referring to the accompanying drawings.

An expanding device 10 according to one embodiment of the present invention is a device for expanding the spacing between bones by inserting a spacer 18 between the bones and expanding the spacer 18 therebetween. The part into which the spacer 18 is to be inserted includes, for example, an interspinal area, a shoulder joint, or an intervertebral disc.

Figure 1:
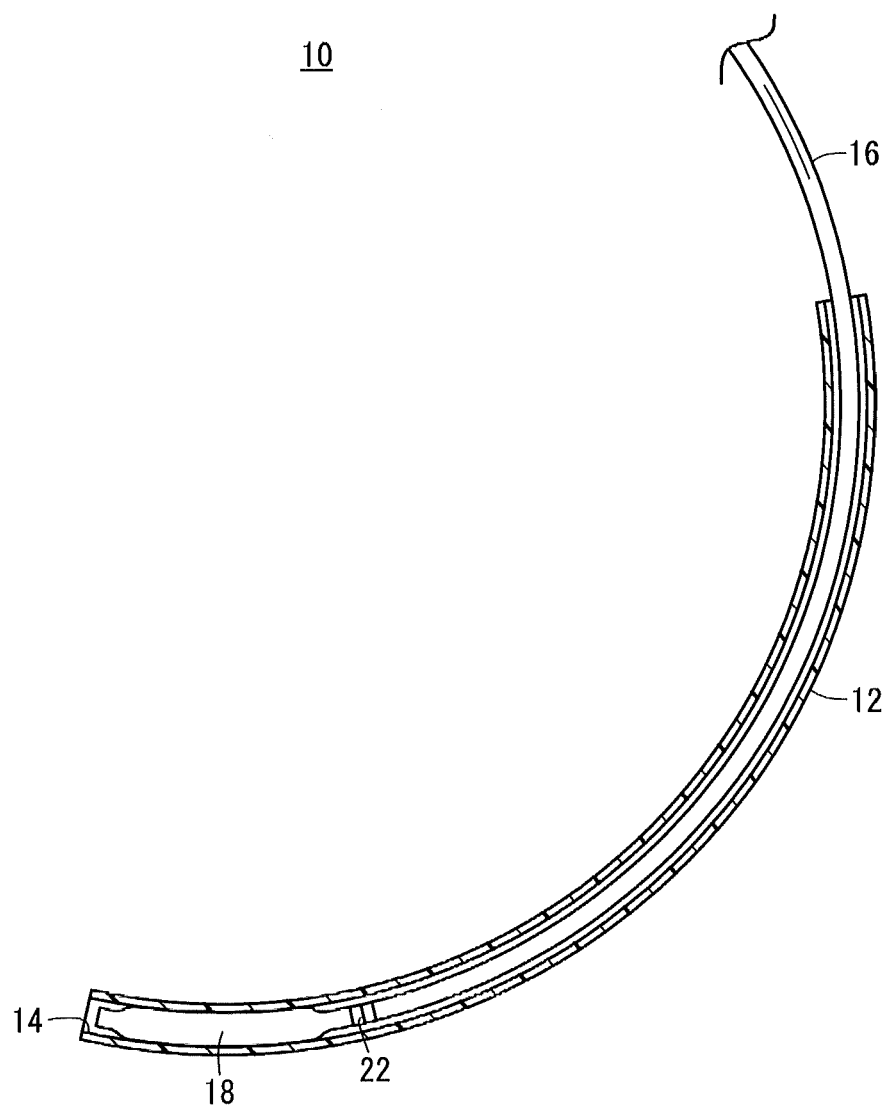
FIG. 1 is a partly sectional plan view of an expanding device according to one embodiment of the present invention.

As shown in FIG. 1, the expanding device 10 includes a hollow arcuate sheath 12, an elongated catheter 16 capable of being inserted and passed in a lumen 14 of the sheath 12, and the spacer 18 provided at a distal end of the catheter 16.

The sheath 12 is configured as an outer needle. Specifically, the sheath 12 can puncture a living body, with an inner needle 20 disposed in the lumen 14 and with the distal end (tip) of the inner needle 20 protruding from the distal end of the sheath 12 by a predetermined length (see FIG. 4A). Incidentally, the inner needle 20 used when the sheath 12 punctures a living body is formed into an arcuate shape with the same radius of curvature as that of the sheath 12, and has a needle tip at a distal end thereof.

The material(s) for forming the sheath 12 and the inner needle 20 is not specifically restricted so long as it is a rigid material having an appropriate strength at such a level as not to be broken or deformed at the time of puncturing a living body. Examples of the material(s) applicable here include metals such as stainless steel, aluminum alloys, cobalt alloys, copper alloys, etc. and rigid resins such as polyvinyl chloride, polyethylene, fluoro-resins, etc. Incidentally, a radiopaque marker may be disposed, for enabling recognition under X-ray radioscopy, at least at a portion of the sheath 12 or the inner needle 20 on the distal-end side.

In the lumen 14 of the sheath 12, the catheter 16 can be inserted and passed, and the spacer 18 in a folded state before expansion can be housed.

The catheter 16 is a flexible (and soft) tube member, and has a lumen through which a filler can be introduced into the spacer 18. To the rear end side (proximal end side) of the catheter 16, there is connected a filler supply source (not shown) such as a syringe, a pump, or the like.

The filler may be a material which is fluid at the time of injection into the spacer 18 and is hardened (solidified) after the injection (for example, bone cement, acrylic resin, binary liquid mixture of cross-linked polymer, etc.), or may be a material which is fluid at the time of injection and remains fluid even after the injection.

The catheter 16 has an appropriate degree of flexibility and an appropriate level of strength (nerve or rigidity) such that the catheter 16 can be inserted and passed in the lumen 14 of the arcuate sheath 12 and that the filler can be introduced into the spacer 18 through the catheter 16. Examples of the material for forming the catheter 16 include polymer materials such as polyolefin, polyvinyl chloride, polyamide, polyamide elastomer, polyurethane, polyurethane elastomer, polyimide, fluoro-resin, silicone resin, etc., mixtures of them, and two or more polymer materials selected from among the above-mentioned polymer materials.

The catheter 16 and the spacer 18 are connected to each other in a separable (disconnectable) manner. A connection structure 22 between the catheter 16 and the spacer 18 may be, for example, a screw engagement structure such that when a torque of not less than a predetermined value is exerted on the catheter 16 and the spacer 18, the screw engagement is released, whereby the catheter 16 and the spacer 18 are separated (disconnected) from each other.

As the connection structure 22, a structure wherein separable connection is achieved by physical engagement (e.g., fitting, catching or the like) and a structure wherein separable connection is based on disconnection of the members by some physical action (e.g., thermal action, chemical action or the like) can be adopted, other than the above-mentioned screw engagement structure.

Figure 2:
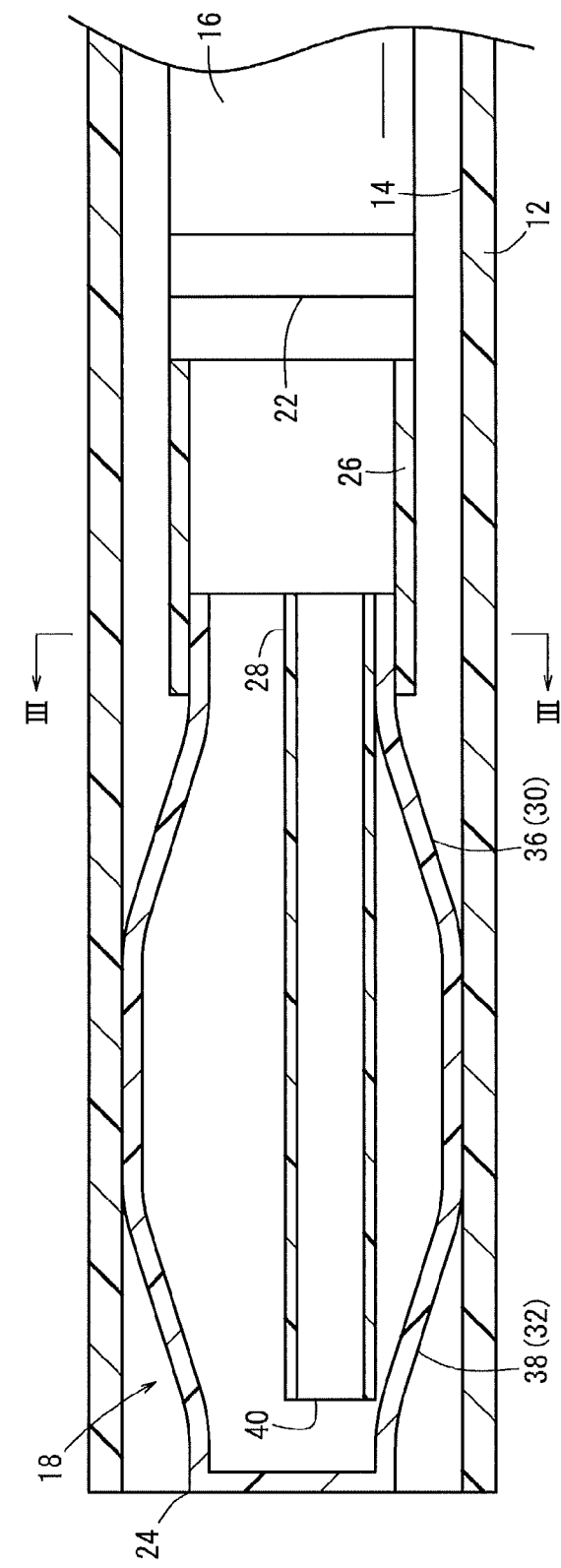
FIG. 2 is a partly-omitted schematic enlarged sectional view of a distal-end side of the expanding device shown in FIG. 1.

As shown in FIG. 2, the spacer 18 includes an expandable spacer body 24, an introduction section 26 through which to introduce a filler into the spacer body 24, and a bypass passage 28 disposed inside the spacer body 24.

The spacer body 24 is configured as a balloon. When contracted, the balloon is folded into a tubular state. When expanded, the spacer body 24 has a structure in which a pair of bulging sections 30 and 32 are interconnected through a constricted section 34 (see FIG. 6). It is preferable that the shape of the spacer body 24 when expanded should be of a dumbbell type, a wheel type (H type) or the like, because the pair of bulging sections 30 and 32 disposed on both sides of the constricted section 34 inserted and passed in an interspinal ligament clamp the spinous processes therebetween.

The material of the spacer body 24 is not specifically restricted, insofar as the material can be expanded upon injection of the filler into the spacer body 24, and the material can endure an external pressure attendant on a movement of a tissue surrounding the spacer body 24, for example, spinous process or interspinal ligament, and a vertebral body. Examples of the applicable material include polyvinyl chloride, polyurethane elastomers, nylons, and PET (polyethylene terephthalate).

The introduction section 26 is for introducing a filler into a rear-end-side (proximal-end-side) expansion section (i.e., a part to be expanded into the bulging section 30) 36. For example, the introduction section 26 is a cylindrical member with a fixed inside diameter, which is formed from the same material as that of the catheter 16. The introduction section 26 is connected to a rear end portion (proximal end portion) of the spacer body 24. Specifically, an outer surface of the rear end portion of the spacer body 24 is secured (adhered) to an inner surface of a distal end portion of the introduction section 26.

The bypass passage 28 is for introducing part of the filler in the introduction section 26 into a distal-end-side (front-end-side) expansion section (i.e., a part to be expanded into the bulging section 32) 38. For example, the bypass passage 28 is a cylindrical member with a fixed inside diameter which is formed from the same material as that of the catheter 16 or from a resin material or the like which is more rigid or flexible than the material of the catheter 16.

A rear end portion of the bypass passage 28 is secured (fixed or adhered) to an inner surface of the rear end portion of the spacer body 24. A distal-end-side opening (outlet) 40 of the bypass passage 28 is located at a distal end portion of the spacer body 24.

Figure 3:
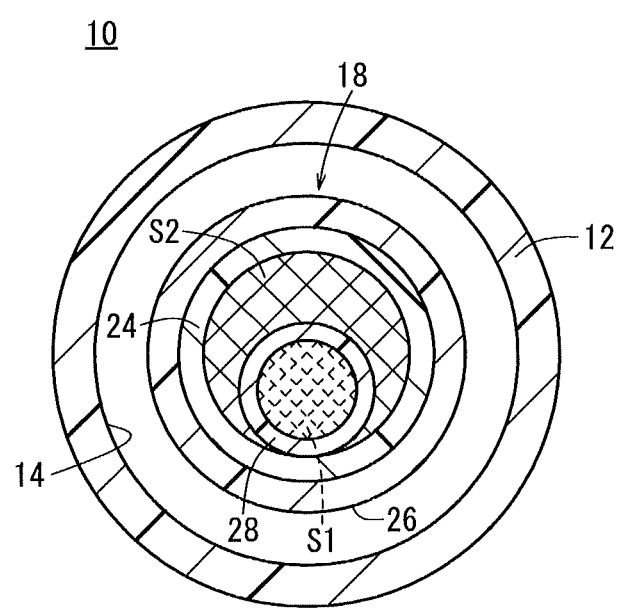
FIG. 3 is a sectional view taken along line III-III of FIG. 2.

As shown in FIG. 3, the spacer body 24 and the bypass passage 28 are so formed that the flow path cross-sectional area (the area of the portion cross-hatched with broken lines in FIG. 3) S1 at the rear end portion of the bypass passage 28 is substantially the same as the flow path cross-sectional area (the area of the portion cross-hatched with solid lines in FIG. 3) S2 on the outside of the bypass passage 28 at the rear end portion of the spacer body 24. Owing thereto, the quantity of the filler introduced into the rear-end-side expansion section 36 through the introduction section 26 per unit time (e.g., per second) and the quantity of the filler introduced into the distal-end-side expansion section 38 through the bypass passage 28 per unit time (e.g., per second) can be substantially equalized.

Taking into account the fluid friction inside the bypass passage 28, the bypass passage 28 may be so formed that the flow path cross-sectional area S1 at the rear end portion of the bypass passage 28 is larger than the flow path cross-sectional area S2 on the outside of the bypass passage 28 at the rear end portion of the spacer body 24. Owing thereto, even where the fluid friction inside the bypass passage 28 is so large that it cannot be ignored, the quantity of the filler introduced into the distal-end-side expansion section 38 through the bypass passage 28 per unit time and the quantity of the filler introduced into the rear-end-side expansion section 36 through the introduction section 26 per unit time can be substantially equalized.

Besides, taking into account the fluid friction inside the bypass passage 28, the bypass passage 28 may be so formed that its inside diameter is gradually increased toward the distal end. This ensures that, even where the fluid friction inside the bypass passage 28 is so large that it cannot be ignored, the quantity of the filler introduced into the distal-end-side expansion section 38 through the bypass passage 28 per unit time and the quantity of the filler introduced into the rear-end-side expansion section 36 through the introduction section 26 per unit time can be substantially equalized.

In addition, the bypass passage 28 has a surface-treated inner surface for reducing the fluid friction inside the bypass passage 28. This ensures that the flow velocity of the filler flowing through the bypass passage 28 can be set higher than the flow velocity of the filler flowing on the outside of the bypass passage 28 at the rear end portion of the spacer body 24. Therefore, the introduction of the filler into the rear-end-side expansion section 36 through the introduction section 26 and the introduction of the filler into the distal-end-side expansion section 38 through the bypass passage 28 can be started substantially simultaneously.

An inner circumferential portion of the bypass passage 28 may be formed from a material showing a comparatively small fluid friction against the filler. Where the bypass passage 28 is configured in this manner, also, the flow velocity of the filler flowing through the bypass passage 28 can be raised.

The expanding device 10 according to the present embodiment is basically configured as above-mentioned. Now, the operation and effect of the expanding device 10 will be described below.

Here, referring mainly to FIGS. 4A to 7, description will be made of a technique of percutaneously inserting the spacer 18 into the space between adjacent spinous processes in a living body and setting the spacer 18 indwelling there by use of the inner needle 20 and the expanding device 10 which have been described above. In FIGS. 4A to 7, reference character B denotes a vertebra, reference character S denotes a spinous process formed at a rear portion of the vertebra B, and reference character L denotes an interspinal ligament formed between the adjacent spinous processes. The same applies also to FIGS. 9A, 9B and 11 which will be described later.

Figure 4C:
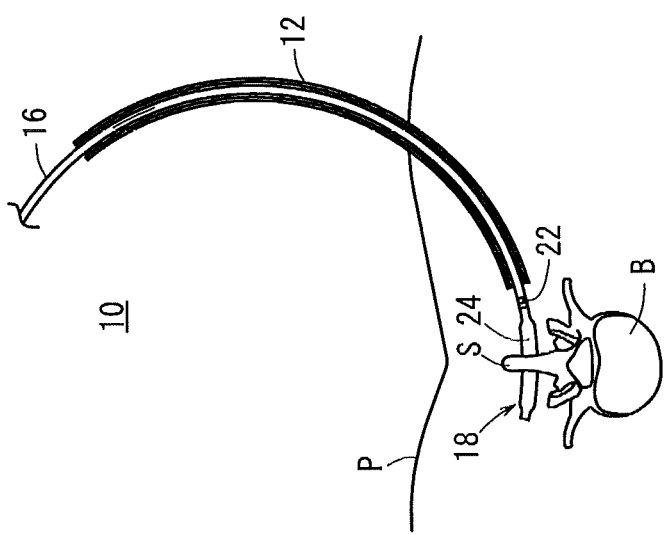
FIG. 4C is an explanatory view illustrating a state in which the whole length of the spacer protrudes from the sheath.

First, a lesion part is determined by an X-ray fluoroscope, MRI (magnetic resonance imaging), ultrasonic diagnostic apparatus or the like, and thereafter the patient P is brought into a prone position. Next, as shown in FIG. 4A, with the inner needle 20 inserted in the sheath 12 of the expanding device 10 such that the needle tip of the inner needle 20 protrudes from the distal end side of the sheath 12, the sheath 12 is made to puncture the patient P, and the sheath 12 and the inner needle 20 are made to penetrate the interspinal ligament between the adjacent spinous processes, in a direction intersecting with the axial direction of the spinal column.

In this case, the puncture is carried out such that a distal end portion of the sheath 12 passes beyond the interspinal space by a predetermined length. After the sheath 12 and the inner needle 20 are made to puncture the patient P by desired lengths, the inner needle 20 is pulled out of the sheath 12, with the sheath 12 being kept in place, i.e., with the sheath 12 left puncturing the patient P, whereby the sheath 12 is left indwelling in situ. In this condition, the sheath 12 is held by the muscles and ligament surrounding the sheath 12.

Figure 4B:
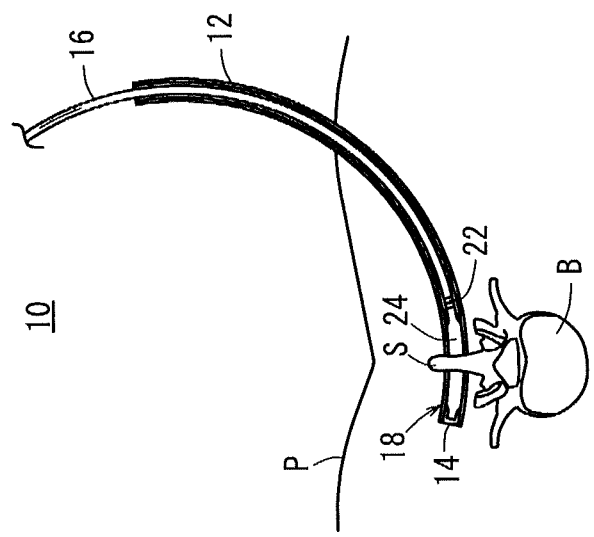
FIG. 4B is an explanatory view illustrating a state in which a spacer constituting the expanding device is disposed on the distal end side of the sheath.
Figure 4A:
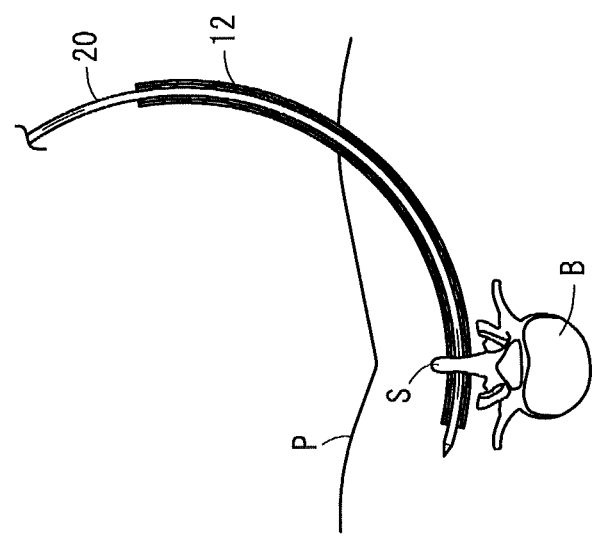
FIG. 4A is an explanatory view illustrating a state in which a distal end portion of a sheath constituting the expanding device is inserted into an interspinal area (between spinous processes)

Next, as shown in FIG. 4B, the catheter 16 equipped with the spacer 18 at the distal end thereof is inserted into the lumen 14 of the sheath 12. Here, the catheter 16 is so inserted that the center of the spacer body 24 in the axial direction is located at the center of the interspinal ligament between the adjacent spinous processes.

After the catheter 16 is inserted to a predetermined position in the sheath 12, the sheath 12 is slid in the rear end direction, with the position of the spacer 18 held unchanged, as shown in FIG. 4C. In this case, the sheath 12 is slid in the rear end direction to such a position that the whole length of the spacer 18 protrudes from the distal end of the sheath 12.

Figure 5A:
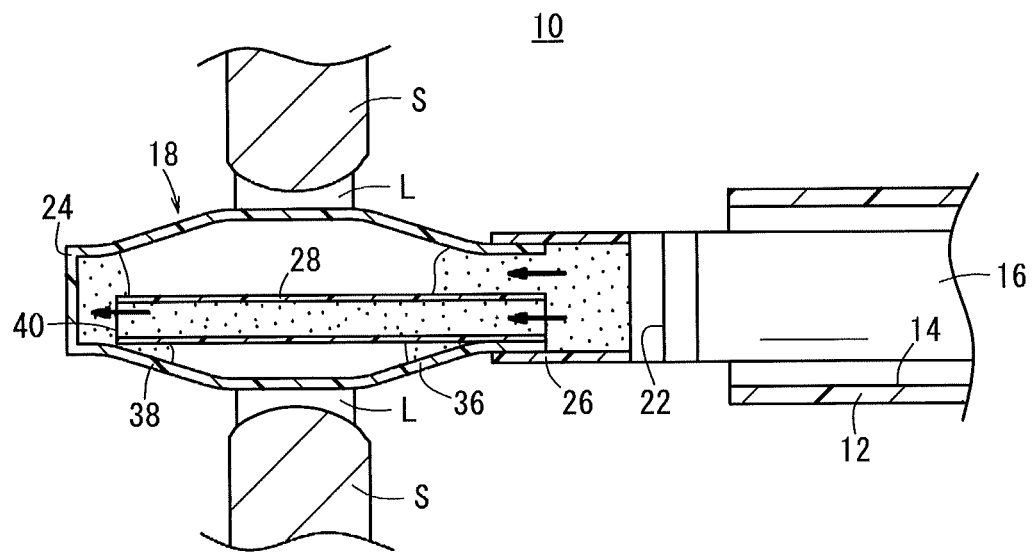
FIG. 5A is a partly-omitted schematic enlarged sectional view for illustrating a state in which a filler is introduced into a distal end portion and a rear end portion of a spacer body shown in FIG. 4C.

Subsequently, the filler supply source (not shown) is operated so as to inject the filler into the spacer 18 through the catheter 16, thereby expanding the spacer body 24. As shown in FIG. 5A, the filler injected from the filler supply source into the introduction section 26 through the catheter 16 flows and branches off into the inside of the bypass passage 28 and into the outside of the bypass passage 28, at the rear end of the spacer body 24.

In this instance, the quantity of the filler flowing through the inside of the bypass passage 28 and the quantity of the filler flowing through the outside of the bypass passage 28 are substantially the same, since the flow path cross-sectional area S1 at the rear end portion of the bypass passage 28 and the flow path cross-sectional area S2 on the outside of the bypass passage 28 at the rear end portion of the spacer body 24 are set substantially equal to each other.

Then, the filler having flowed into the inside of the bypass passage 28 flows out via the distal-end-side opening 40 of the bypass passage 28 into a distal end portion of the spacer body 24, to be guided into the distal-end-side expansion section 38. On the other hand, the filler having flowed into the outside of the bypass passage 28 at the rear end portion of the spacer body 24 is guided into the rear-end-side expansion section 36.

In the present embodiment, the fluid friction inside the bypass passage 28 is reduced by a surface treatment of the inner surface of the bypass passage 28. Consequently, the introduction of the filler into the distal-end-side expansion section 38 through the bypass passage 28 and the introduction of the filler into the rear-end-side expansion section 36 through the introduction section 26 can be started substantially simultaneously.

In addition, as above-mentioned, the quantity of the filler flowing into the inside of the bypass passage 28 and the quantity of the filler flowing into the outside of the bypass passage 28 at the rear end portion of the spacer body 24 are substantially the same. Thus, the quantity of the filler introduced into the distal-end-side expansion section 38 per unit time and the quantity of the filler introduced into the rear-end-side expansion section 36 per unit time are substantially the same.

Figure 5B:
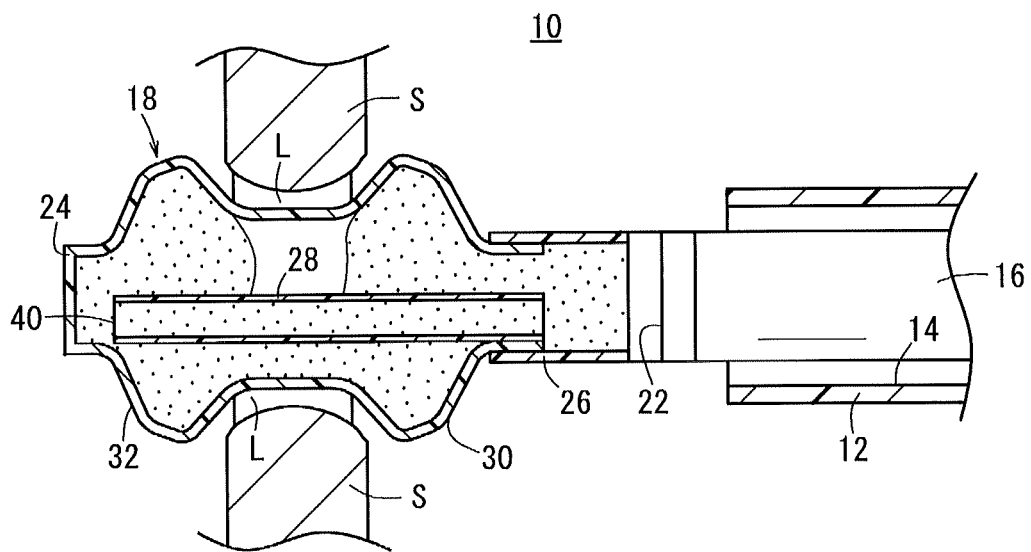
FIG. 5B is a partly-omitted schematic enlarged sectional view for illustrating a state in which a distal-end-side expansion section and a rear-end-side expansion section of the spacer body are filled with the filler.

Therefore, when the filler is introduced into the distal-end-side expansion section 38 and the rear-end-side expansion section 36, as shown in FIG. 5B, the left side and the right side of the spacer body 24 are expanded substantially simultaneously and substantially symmetrically, thereby to form a pair of bulging sections 30 and 32. In other words, in the present embodiment, a situation is avoided in which either one of a distal-end-side portion and a rear-end-side portion of the spacer body 24 is expanded in advance of the other, causing the spacer body 24 to be displaced out of position with respect to the spinous processes.

Figure 6:
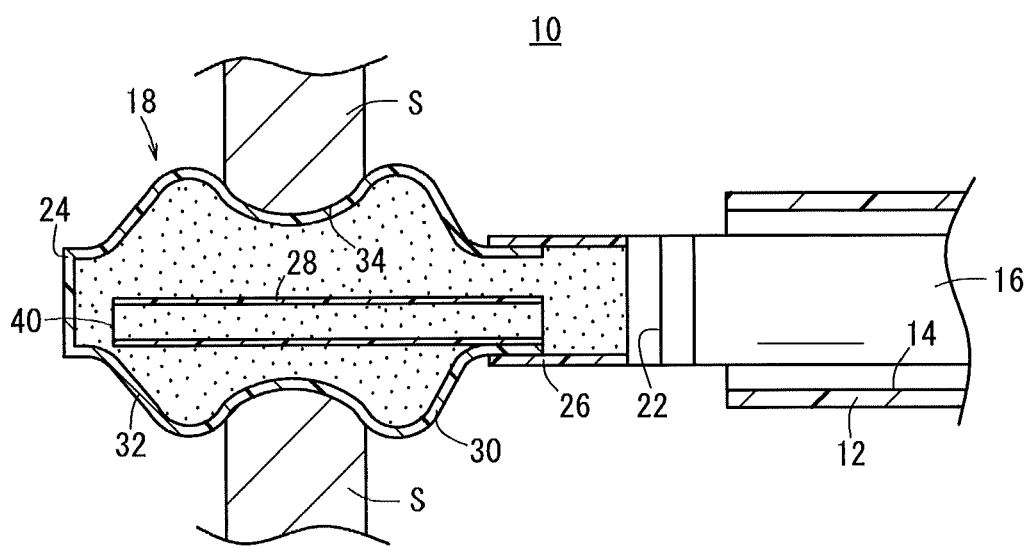
FIG. 6 is a partly-omitted schematic enlarged sectional view for illustrating a state in which filling of the spacer body with the filler is completed.

Thereafter, as shown in FIG. 6, the filler flows into a central portion of the spacer body 24 from both sides of the spacer body 24. As a result, the constricted section 34 interconnecting the pair of bulging sections 30 and 32 is expanded, and the spacing between the spinous processes is accordingly expanded, resulting in a state wherein the spacer body 24 is prevented from slipping off from the interspinal ligament between the spinous processes.

Figure 7:
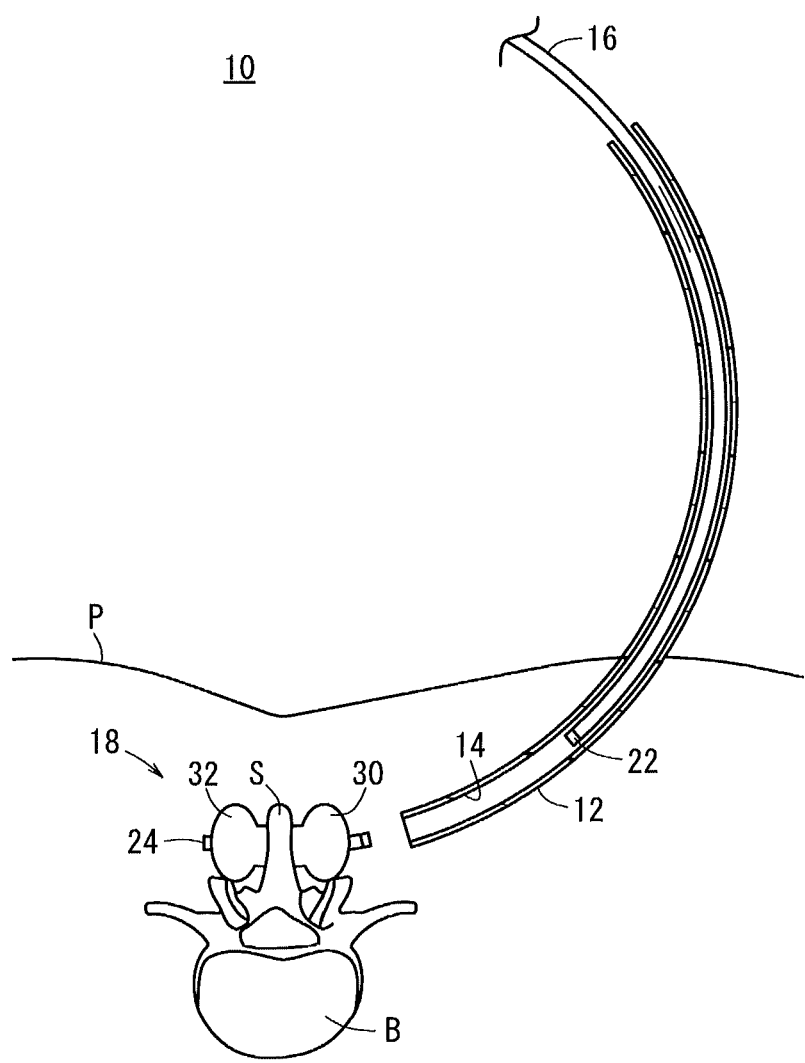
FIG. 7 is an explanatory view illustrating a state in which a catheter of the expanding device is detached from the spacer.

After the spacer body 24 is expanded, the catheter 16 is detached from the spacer 18, as shown in FIG. 7. In the case where the connection structure 22 between the spacer 18 and the catheter 16 is a screw engagement structure, rotation of the catheter 16 about its axis causes only the catheter 16 to be rotated, without rotation of the spacer 18 inserted in the interspinal ligament between the adjacent spinous processes, so that the screw engagement between the spacer 18 and the catheter 16 is released. Thus, the catheter 16 can be detached from the spacer 18.

Incidentally, in the case where the filler is a material which is fluid at the time of injection thereof and is hardened (solidified) after the injection, it is preferable to separate the spacer 18 and the catheter 16 after the filler has been hardened. Alternatively, where the filler is a material which remains fluid even after the injection thereof, it is preferable to provide a back-flow preventive structure (e.g., check valve) at the inlet of the spacer 18.

After the catheter 16 is detached from the spacer 18, the catheter 16 is pulled out of the sheath 12, and then the sheath 12 is completely pulled out of the patient P. Thus, the spacer 18 is left indwelling between the spinous processes.

As above-mentioned, according to the present embodiment, the filler can be introduced through the introduction section 26 into the rear-end-side expansion section 36 of the spacer body 24, and, simultaneously, part of the filler in the introduction section 26 can be introduced through the bypass passage 28 into the distal-end-side expansion section 38 of the spacer body 24. Therefore, the distal-end-side portion and the rear-end-side portion of the spacer body 24 can be expanded substantially simultaneously. In other words, it is possible to prevent either one of the distal-end-side portion and the rear-end-side portion of the spacer body 24 from being expanded in advance of the other. This makes it possible to prevent the spacer body 24 (spacer 18) from being displaced out of position with respect to the spinous processes. Consequently, the spacing between the spinous processes can be expanded reliably.

The inner surface of the bypass passage 28 is subjected to the surface treatment, whereby it is ensured that the introduction of the filler into the rear-end-side expansion section 36 of the spacer body 24 through the introduction section 26 and the introduction of the filler into the distal-end-side expansion section 38 of the spacer body 24 through the bypass passage 28 are started substantially simultaneously. Further, the flow path cross-sectional area S1 at the rear end portion of the bypass passage 28 and the flow path cross-sectional area S2 on the outside of the bypass passage 28 at the rear end portion of the spacer body 24 are set substantially the same (in the case where the fluid friction inside the bypass passage 28 is so large that it cannot be ignored, the bypass passage 28 is so configured that the flow path cross-sectional area S1 at the rear end portion of the bypass passage 28 is greater than the flow path cross-sectional area S2 on the outside of the bypass passage 28 at the rear end portion of the spacer body 24, or the bypass passage 28 is so configured that its inside diameter is gradually increased toward the distal end), whereby it is ensured that the quantity of the filler introduced into the rear-end-side expansion section 36 through the introduction section 26 per unit time and the quantity of the filler introduced into the distal-end-side expansion section 38 through the bypass passage 28 per unit time are substantially the same. Thus, the distal-end-side portion and the rear-end-side portion (i.e., left side and right side as shown in FIG. 5B) of the spacer body 24 can be expanded substantially simultaneously and substantially symmetrically. Consequently, the spacer 18 can be suitably restrained from being displaced out of place with respect to the spinous processes.

Furthermore, since the introduction section 26 is connected to the rear end portion of the spacer body 24 and the distal-end-side opening 40 of the bypass passage 28 is located at the distal end portion of the spacer body 24, the filler can be reliably introduced into the rear-end-side expansion section 36 through the introduction section 26, and the filler can be reliably introduced also into the distal-end-side expansion section 38 through the bypass passage 28.

In the present embodiment, since the bypass passage 28 is disposed inside the spacer body 24, an increase in the size of the spacer 18 can be suppressed, as compared with the case where the bypass passage 28 is disposed outside of the spacer body 24.

Furthermore, since the rear end portion of the bypass passage 28 is secured to the rear end portion of the spacer body 24 which is comparatively less deformed at the time of expansion of the spacer body 24, displacement of the bypass passage 28 within the spacer body 24 can be restrained or prevented. In addition, detachment of the bypass passage 28 from the spacer body 24 during introduction of the filler into the spacer body 24 can be suitably prevented. Consequently, the filler can be reliably introduced into the distal-end-side expansion section 38 of the spacer body 24 through the bypass passage 28.

(First Modification)

Next, a spacer 18a according to a first modification of the present invention will be described below with reference to FIG. 8A. Incidentally, in the spacer 18a according to this modification, elements exhibiting identical or similar functions and effects to those in the above-described spacer 18 are denoted by the same reference symbols as used above, and detailed descriptions of such elements will be omitted. The same applies also to spacers 18b to 18j according to second to tenth modifications which will be described later.

Figure 8A:
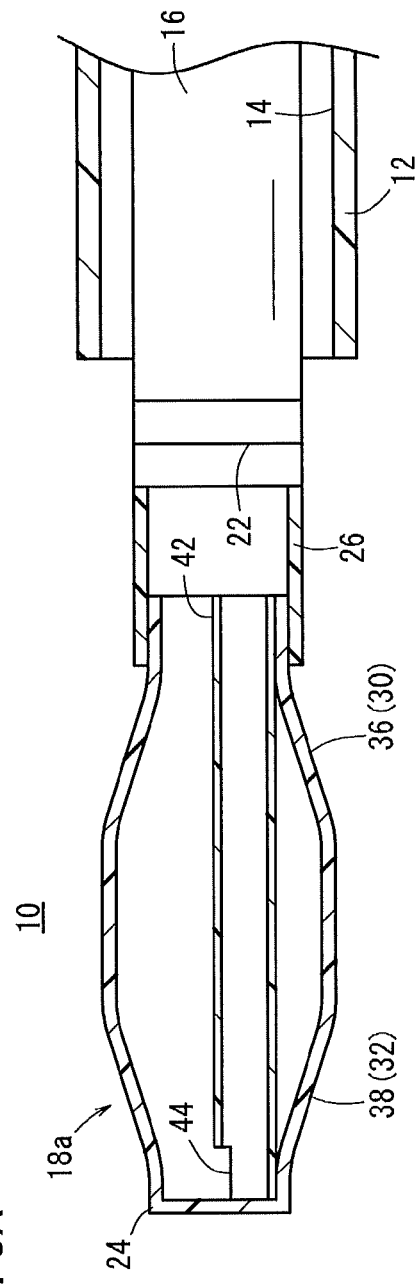
FIG. 8A is a partly-omitted schematic enlarged sectional view of an expanding device including a spacer according to a first modification of the present invention.

As shown in FIG. 8A, the spacer 18a according to this modification is provided with a bypass passage 42 in place of the above-described bypass passage 28. The bypass passage 42 extends to the distal end of the spacer body 24, and a distal end portion of the bypass passage 42 is secured (fixed, adhered) to an inner surface of a distal end portion of the spacer body 24.

Specifically, the bypass passage 42 is secured to the distal end portion and a rear end portion of the spacer body 24 which are comparatively less deformed at the time of expansion of the spacer body 24. Therefore, detachment of the bypass passage 42 from the spacer body 24 during introduction of the filler into the spacer body 24 can be suitably prevented.

In addition, a wall part of the distal end portion of the bypass passage 42 is formed with a cutout (outlet) 44. This enables a filler having flowed through the bypass passage 42 to flow out through the cutout 44 into the distal end portion of the spacer body 24.

(Second Modification)

Figure 8B:
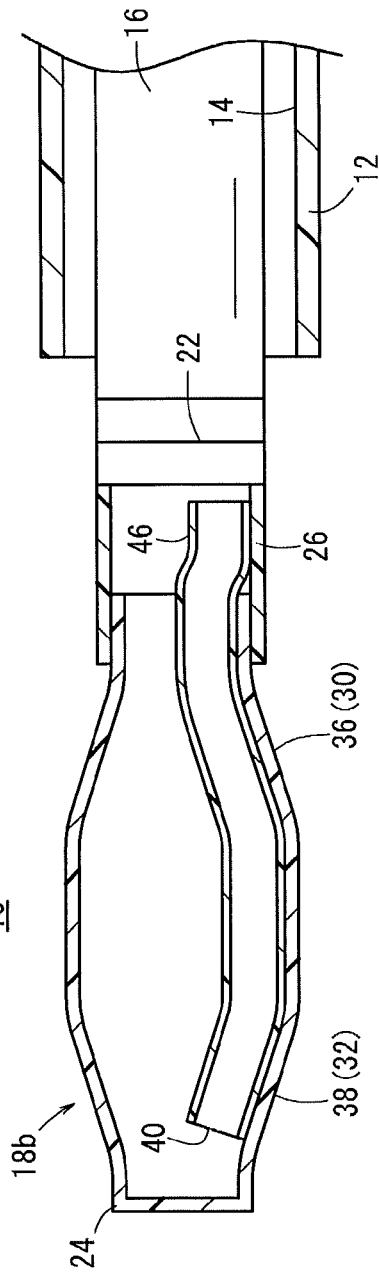
FIG. 8B is a partly-omitted schematic enlarged sectional view of an expanding device including a spacer according to a second modification of the present invention.

Next, a spacer 18b according to a second modification of the present invention will be described below with reference to FIG. 8B. As shown in FIG. 8B, the spacer 18b according to this modification is provided with a bypass passage 46 in place of the above-described bypass passage 28.

The bypass passage 46 is configured to be more flexible than the catheter 16 and the introduction section 26 (more flexible than the above-mentioned bypass passage 28). In other words, the bypass passage 46 is configured to be flexible to such an extent that it can be deformed along the shape of the spacer body 24. In addition, the bypass passage 46 extends to a rear end portion of the introduction section 26, and a portion of the bypass passage 46 that is located inside the spacer body 24 is secured (fixed, adhered) to the inner surface of the spacer body 24 over the whole length of the portion.

According to this modification, the portion of the bypass passage 46 that is located inside the spacer body 24 is secured to the inner surface of the spacer body 24 over substantially the whole length of the portion. Therefore, the area of securing (area of adhesion) between the bypass passage 46 and the spacer body 24 can be easily enlarged. This enables the bypass passage 46 to be secured to the spacer body 24 more firmly. Consequently, detachment of the bypass passage 46 from the spacer body 24 during introduction of the filler into the spacer body 24 can be suitably prevented.

In addition, since the bypass passage 46 is configured to be flexible, when the spacer body 24 is expanded, the shape of the bypass passage 46 can be deformed along the shape of the expanded spacer body 24. Consequently, it is possible to effectively prevent the bypass passage 46 from hampering the expansion of the spacer body 24.

(Third Modification)

Figure 9A:
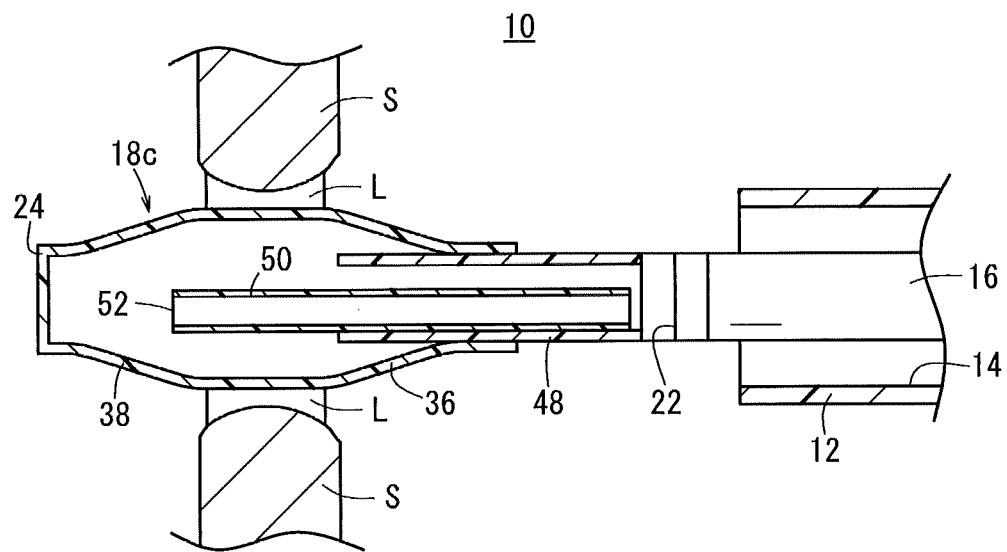
FIG. 9A is a partly-omitted schematic enlarged sectional view of an expanding device including a spacer according to a third modification of the present invention.
Figure 9B:
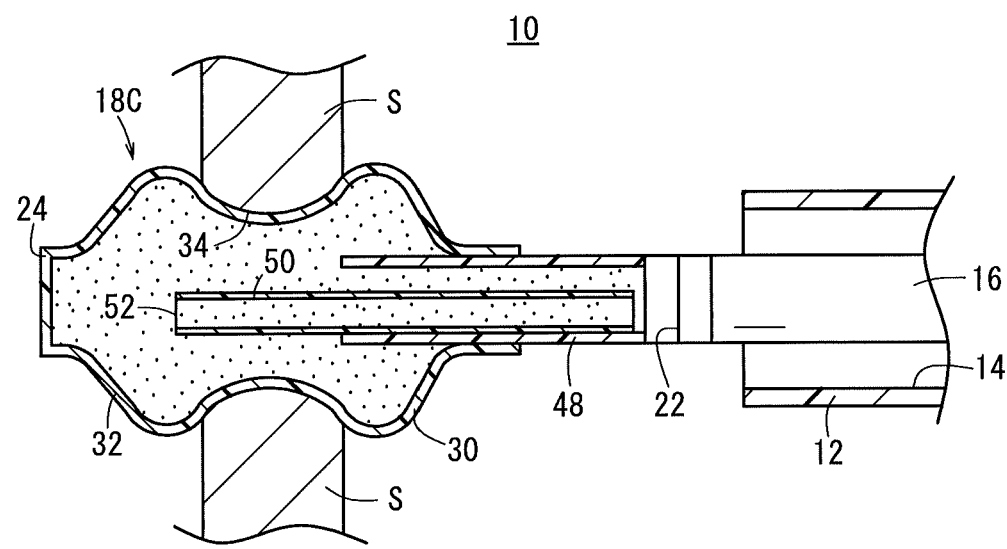
FIG. 9B is a partly-omitted schematic enlarged sectional view illustrating a state in which a spacer body of the spacer is filled with a filler.

Next, a spacer 18c according to a third modification of the present invention will be described below with reference to FIGS. 9A and 9B. As shown in FIGS. 9A and 9B, the spacer 18c in this modification is provided with an introduction section 48 and a bypass passage 50 in place of the introduction section 26 and the bypass passage 28 which have been described above.

The introduction section 48 extends to the rear-end-side expansion section 36 in the spacer body 24. Specifically, the distal end of the introduction section 48 is located at a distal end portion (i.e., a portion that is adjacent to the rear-end side of a portion to be expanded into the constricted section 34) of the rear-end-side expansion section 36.

The bypass passage 50 extends from a rear end portion of the introduction section 48 to the distal-end-side expansion section 38. Specifically, a distal end opening (outlet) 52 of the bypass passage 50 is located at a rear end portion (i.e., a portion that is adjacent to the distal-end side of a portion to be expanded into the constricted section 34) of the distal-end-side expansion section 38.

According to this modification, the introduction section 48 extends to the rear-end-side expansion section 36 in the spacer body 24, and the distal end opening 52 of the bypass passage 50 is located at the distal-end-side expansion section 38. Therefore, the filler can be assuredly introduced into the rear-end-side expansion section 36 through the introduction section 48, and the filler can be reliably introduced into the distal-end-side expansion section 38 through the distal-end-side opening 52 of the bypass passage 50.

(Fourth Modification)

Figure 10:
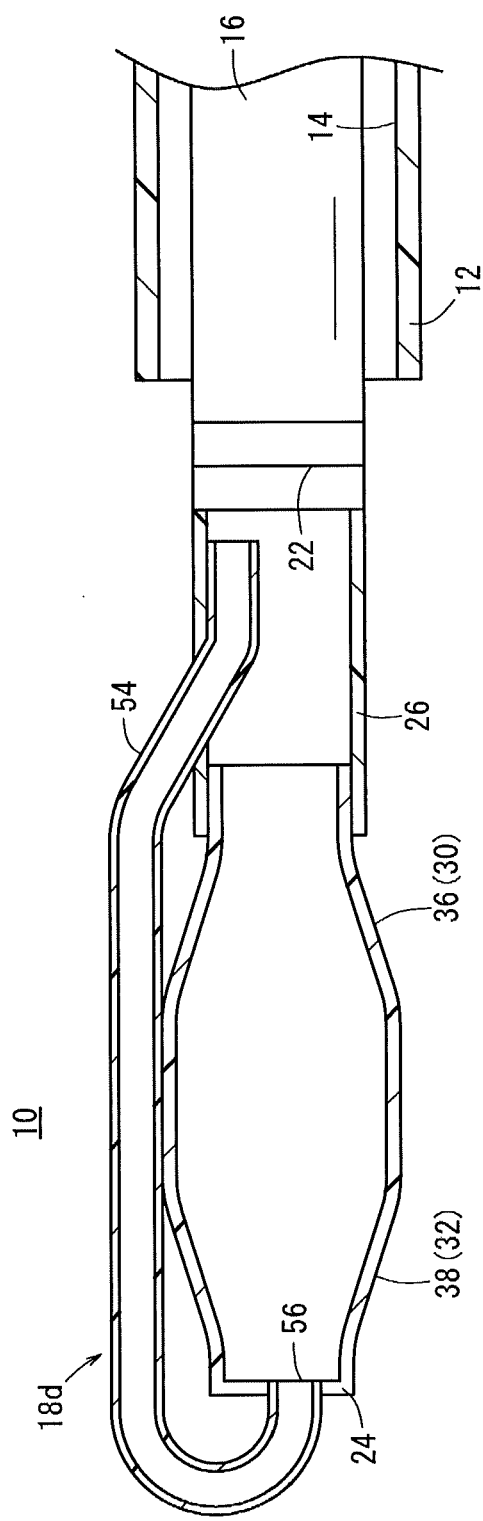
FIG. 10 is a partly-omitted schematic enlarged sectional view of an expanding device including a spacer according to a fourth modification of the present invention.
Figure 11:
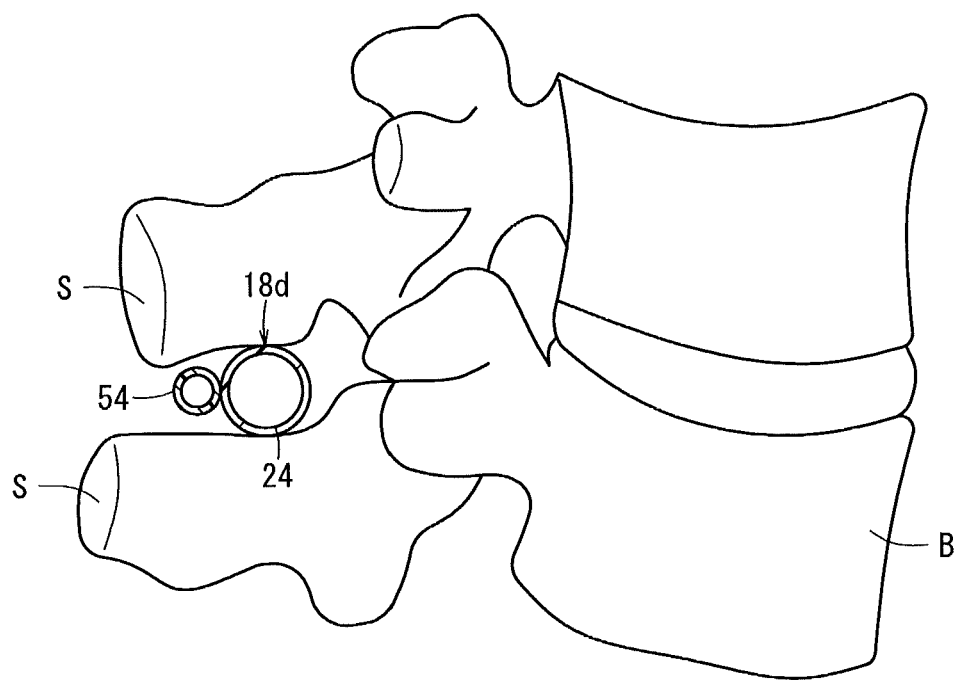
FIG. 11 is a partly-omitted schematic sectional view for illustrating a positional relationship between a bypass passage constituting the spacer shown in FIG. 10 and spinous processes.

Next, a spacer 18d according to a fourth modification of the present invention will be described below with reference to FIGS. 10 and 11. As shown in FIG. 10, the spacer 18d according to this modification is provided with a bypass passage 54 in place of the above-described bypass passage 28.

The bypass passage 54 is configured to be more flexible than the catheter 16 and the introduction section 26 (more flexible than the above-described bypass passage 28). In other words, the bypass passage 54 is configured to be flexible to such an extent that it can be deformed along the shape of the spacer body 24. In addition, the bypass passage 54 is secured (fixed, adhered) to an outer surface of the spacer body 24 in the state of being located outside of the spacer body 24.

The bypass passage 54 includes a rear end portion located inside a rear end portion of the introduction section 26, and a distal end portion connected to the distal end of the spacer body 24. As understood from FIG. 10, a distal-end-side opening (outlet) 56 of the bypass passage 54 faces toward the rear end.

According to this modification, the bypass passage 54 is disposed outside of the spacer body 24, so that the configuration of the spacer 18d can be simplified as compared with the case where the bypass passage 54 is disposed inside the spacer body 24.

In addition, since the bypass passage 54 is secured to the outer surface of the spacer body 24, the bypass passage 54 can be restrained from being caught on tissues around the spacer body 24. Furthermore, since the bypass passage 54 is configured to be flexible (is soft), it is possible to effectively prevent the bypass passage 54 from hampering expansion of the spacer body 24.

In the case of using the spacer 18d according to this modification, for example, it is preferable that a mark indicative of the position of the bypass passage 54 in the circumferential direction of the catheter 16 is provided at a rear-end-side portion of the catheter 16. Based on the mark, the user or the like rotates the catheter 16 such that the bypass passage 54 and spinous processes do not interfere with each other, to thereby dispose the spacer 18d between the spinous processes, whereby the spacing between the spinous processes can be assuredly expanded by the spacer 18d (see FIG. 11).

(Fifth Modification)

Figure 12A:
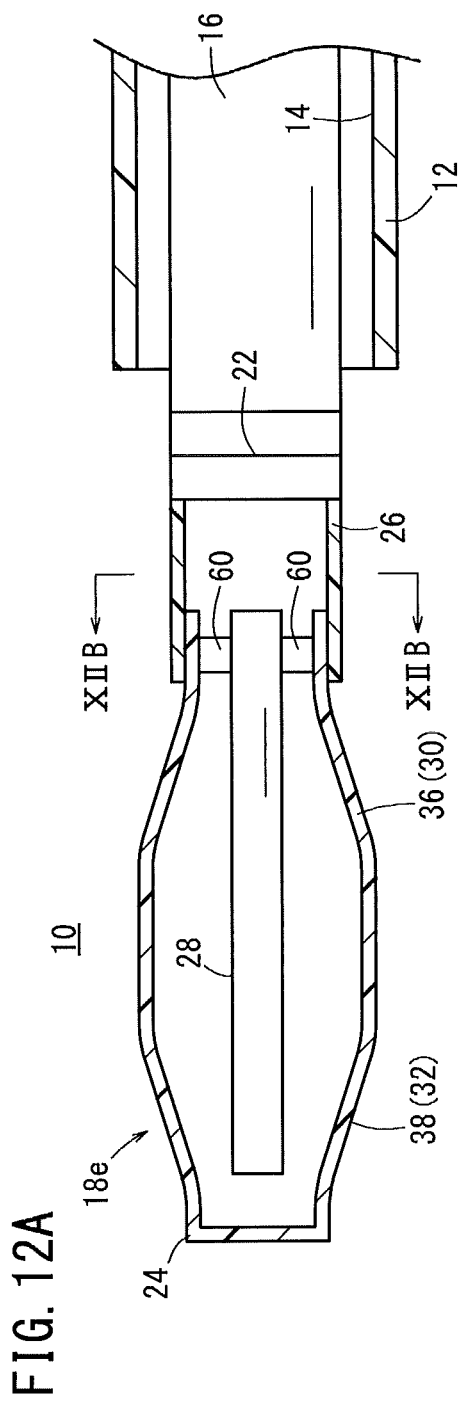
FIG. 12A is a partly-omitted schematic sectional view of an expanding device including a spacer according to a fifth modification of the present invention.
Figure 12B:
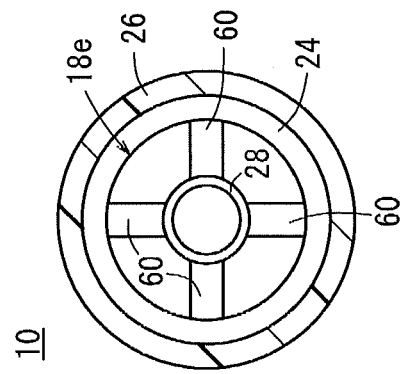
FIG. 12B is a sectional plan view of a bypass passage, a fixation section, and the like taken along line XIIB-XIIB of FIG. 12A, as viewed from the proximal end side.

Next, a spacer 18e according to a fifth modification of the present invention will be described below with reference to FIGS. 12A and 12B. As shown in FIGS. 12A and 12B, the spacer 18e according to this modification is provided with plural (in this modification, four) fixing parts 60 for fixing the bypass passage 28.

The fixing parts 60 are for fixing the bypass passage 28 to the spacer body 24 such that the axis of the bypass passage 28 is located on the axis of the spacer body 24, and are secured to a rear end portion of the bypass passage 28 at regular intervals along the circumferential direction of the bypass passage 28. In addition, the fixing parts 60 are secured to the inner surface of the rear end portion of the spacer body 24. In the case where the thus-configured spacer 18e is used, also, the effects obtained in the above-described embodiment can be obtained.

(Sixth Modification)

Figure 13:
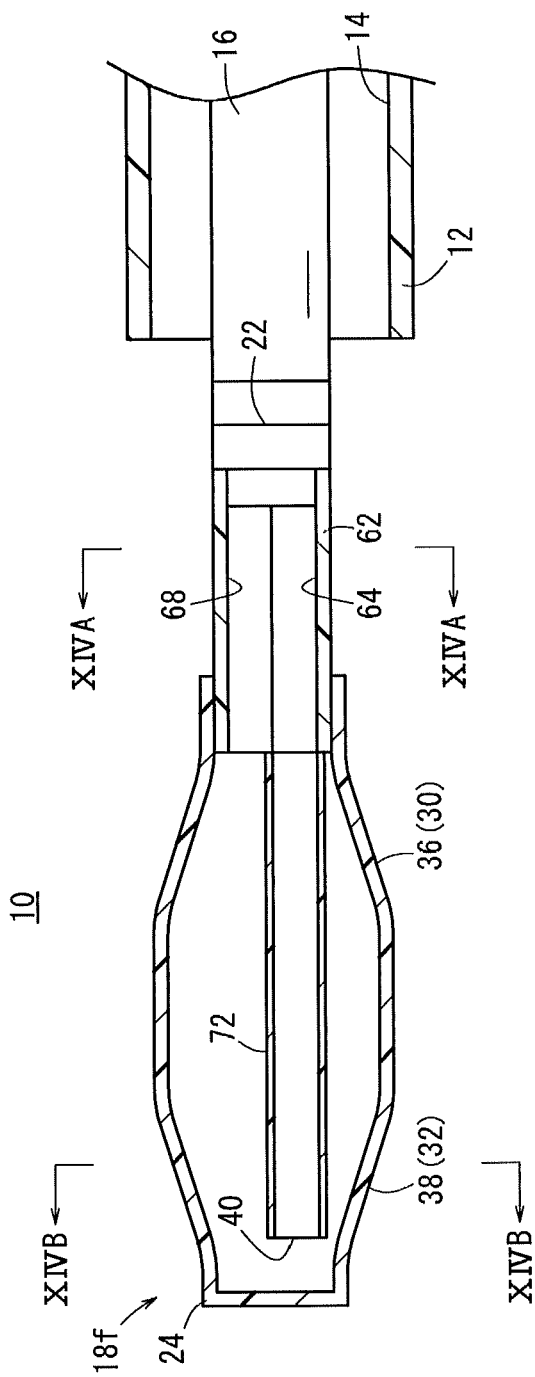
FIG. 13 is a partly-omitted schematic enlarged sectional view of an expanding device including a spacer according to a sixth modification of the present invention.
Figure 14A:
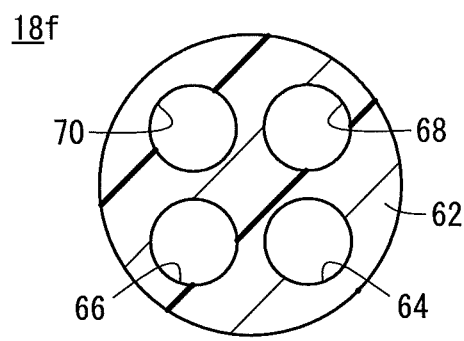
FIG. 14A is a sectional view taken along line XIVA-XIVA of FIG. 13.
Figure 14B:
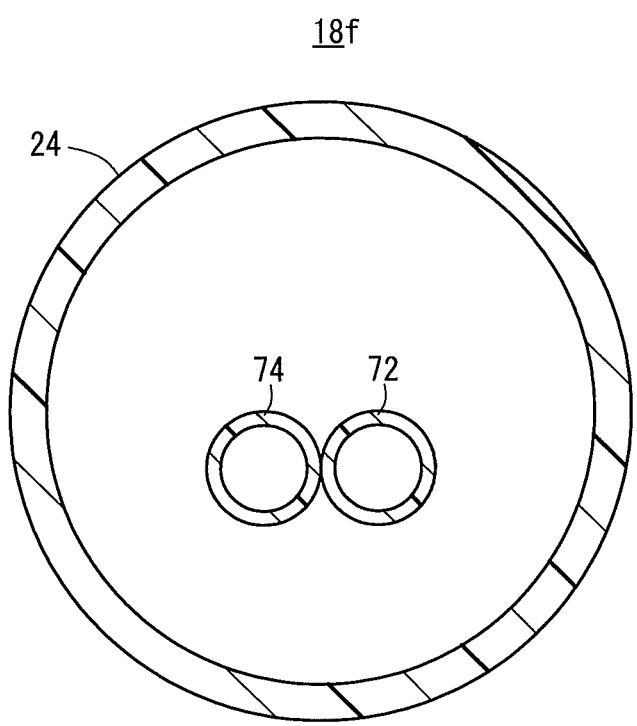
FIG. 14B is a sectional view taken along line XIVB-XIVB of FIG. 13.

Next, a spacer 18f according to a sixth modification of the present invention will be described below with reference to FIGS. 13 to 14B. As shown in FIGS. 13 to 14B, the spacer 18f according to this modification is provided with an introduction section 62 in place of the above-described introduction section 26.

The introduction section 62 is formed with plural (in this modification, four) circular introduction holes (lumens) 64, 66, 68, and 70 through which a filler flows. The flow path cross-sectional areas of the introduction holes 64, 66, 68, and 70 may be set arbitrarily; for example, they may be set to be the same.

In addition, the spacer 18f according to this modification is provided with two bypass passages 72 and 74. The bypass passages 72 and 74 each have a circular lumen with a flow path cross-sectional area equal to that of each of the introduction holes 64, 66, 68, and 70. The bypass passage 72 is secured to the distal end face of the introduction section 62 so as to communicate with the introduction hole 64, whereas the bypass passage 74 is secured to the distal end face of the introduction section 62 so as to communicate with the introduction hole 66. Incidentally, each of the bypass passages 72 and 74 may be formed integrally with the introduction section 62.

According to this modification, the filler having flowed through the introduction holes 68 and 70 is introduced into the rear-end-side expansion section 36 of the spacer body 24, whereas the filler having flowed through the introduction holes 64 and 66 and the bypass passages 72 and 74 is introduced into the distal-end-side expansion section 38 of the spacer body 24. Therefore, in the case where the spacer 18f according to this modification is used, also, the same effects as those obtained in the above-described embodiment can be obtained.

(Seventh Modification)

Figure 15:
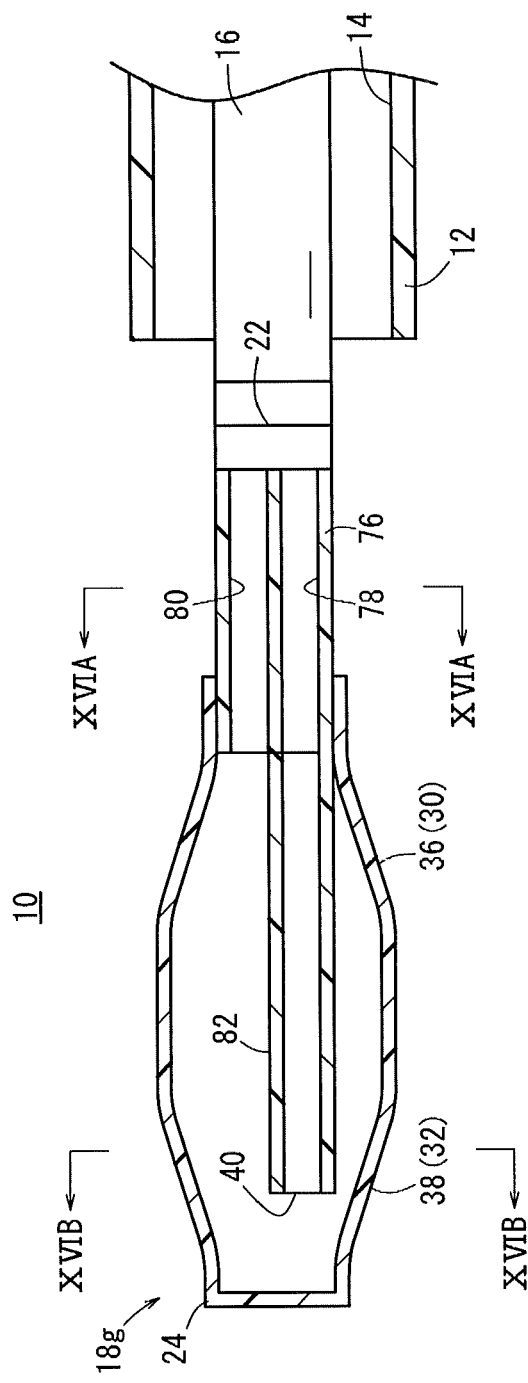
FIG. 15 is a partly-omitted schematic enlarged sectional view of an expanding device including a spacer according to a seventh modification of the present invention.
Figure 16A:
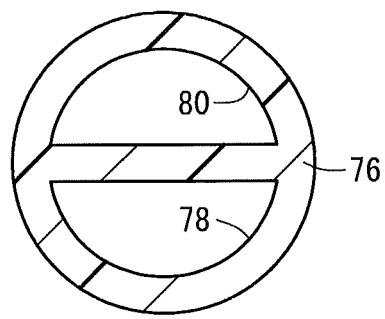
FIG. 16A is a sectional view taken along line XVIA-XVIA of FIG. 15.
Figure 16B:
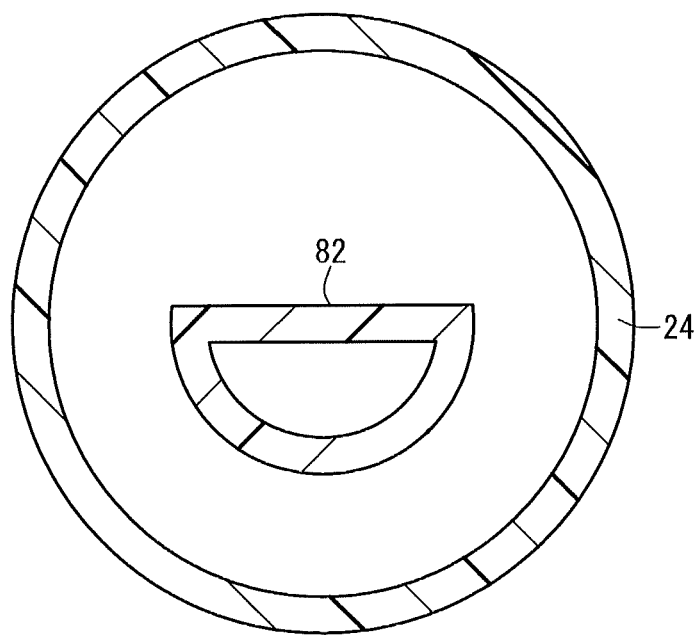
FIG. 16B is a sectional view taken along line XVIB-XVIB of FIG. 15.

Next, a spacer 18g according to a seventh modification of the present invention will be described below with reference to FIGS. 15 to 16B. As shown in FIGS. 15 to 16B, the spacer 18g according to this modification is provided with an introduction section 76 in place of the above-described introduction section 26.

The introduction section 76 is provided with plural (in this modification, two) semicircular introduction holes (lumens) 78 and 80 through which a filler flows. The flow path cross-sectional areas of the introduction holes 78 and 80 may be set arbitrarily; for example, they may be set to be the same.

In addition, the spacer 18g according to this modification is formed with a bypass passage 82 in place of the above-described bypass passage 28. The bypass passage 82 has a semicircular lumen with a flow path cross-sectional area equal to that of each of the introduction holes 78 and 80. The bypass passage 82 is secured to the distal end face of the introduction section 76 so as to communicate with the introduction hole 78. Incidentally, the bypass passage 82 and the introduction section 76 may be integrally formed.

According to this modification, the filler having flowed through the introduction hole 80 is introduced into the rear-end-side expansion section 36 of the spacer body 24, whereas the filler having flowed through the introduction hole 78 and the bypass passage 82 is introduced into the distal-end-side expansion section 38 of the spacer body 24. Therefore, in the case where the spacer 18g according to this modification is used, also, the same effects as those obtained in the above-described embodiment can be obtained.

(Eighth Modification)

Figure 17:
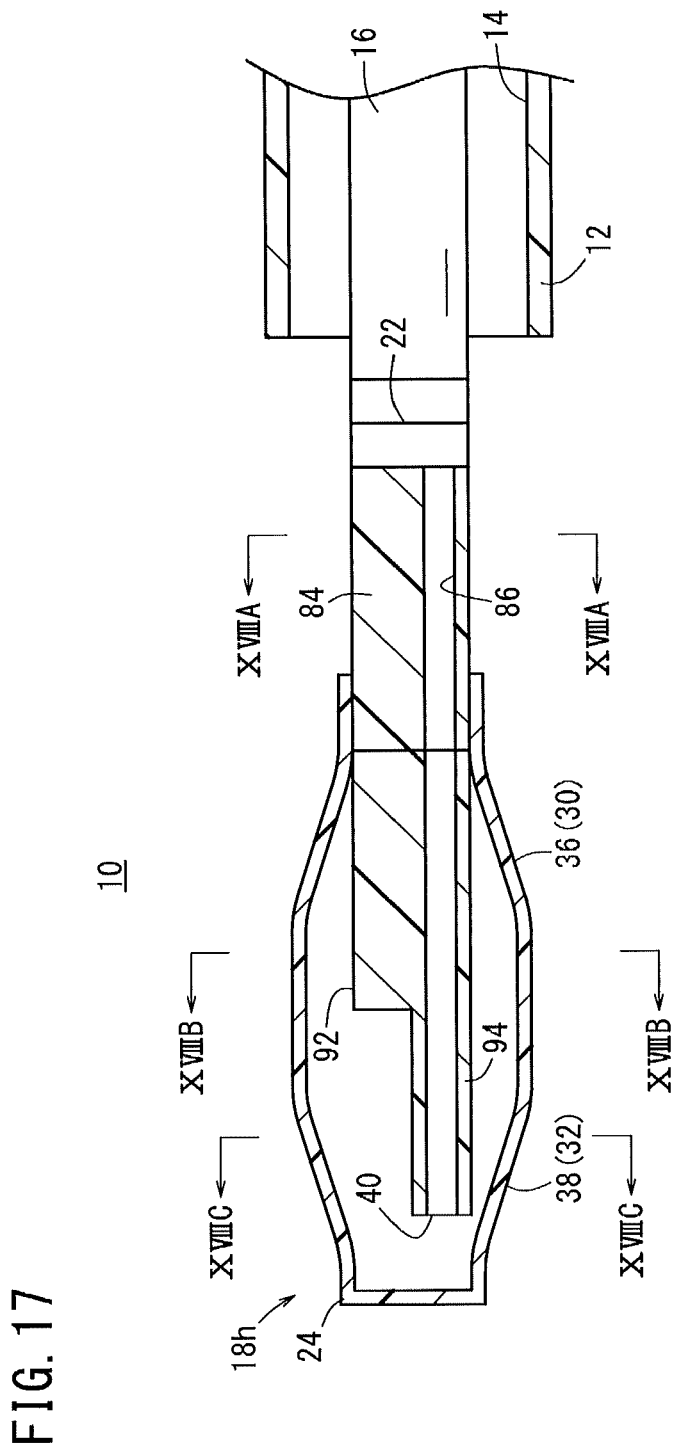
FIG. 17 is a partly-omitted schematic enlarged sectional view of an expanding device including a spacer according to an eighth modification of the present invention.

Next, a spacer 18h according to an eighth modification of the present invention will be described below with reference to FIGS. 17 to 18C. As shown in FIGS. 17 to 18C, the spacer 18h according to this modification is provided with an introduction section 84 in place of the above-described introduction section 26.

Figure 18A:
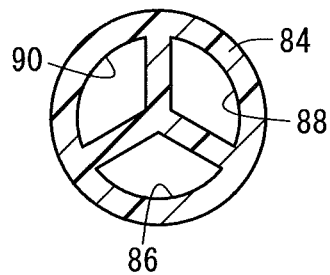
FIG. 18A is a sectional view taken along line XVIIIA-XVIIIA of FIG. 17.
Figure 18B:
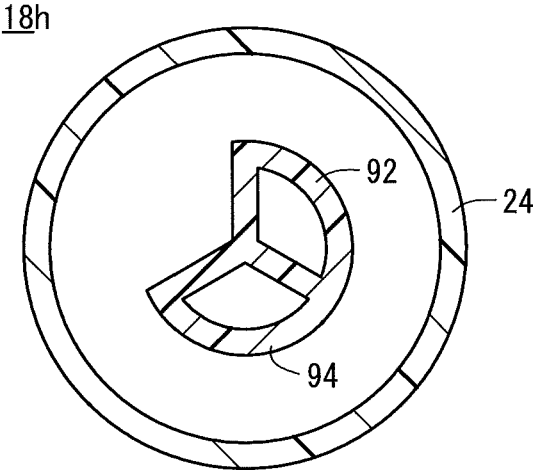
FIG. 18B is a sectional view taken along line XVIIIB-XVIIIB of FIG. 17.
Figure 18C:
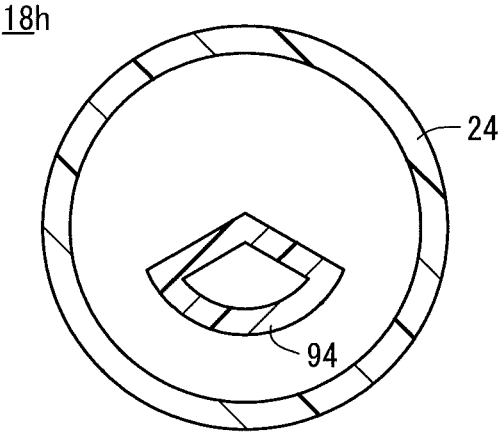
FIG. 18C is a sectional view taken along line XVIIIC-XVIIIC of FIG. 17.

As understood from FIG. 18A, the introduction section 84 is formed with plural (in this modification, three) sector-shaped introduction holes (lumens) 86, 88, and 90 through which a filler flows. The flow path cross-sectional areas of the introduction holes 86, 88, and 90 may be set arbitrarily; for example, they may be set to be the same.

In addition, the spacer 18h according to this modification is additionally provided with a communication passage 92, and is provided with a bypass passage 94 in place of the above-described bypass passage 28. The communication passage 92 and the bypass passage 94 are formed integrally, and each have a sector-shaped lumen with a flow path cross-sectional area equal to that of each of the introduction holes 86, 88, and 90.

The communication passage 92 is secured to the distal end face of the introduction section 84 so as to communicate with the introduction hole 88. The distal end of the communication passage 92 is located at substantially the center of the spacer body 24 in the axial direction. The bypass passage 94 is secured to the distal end face of the introduction section 84 so as to communicate with the introduction hole 86. Incidentally, the introduction section 84, the communication passage 92, and the bypass passage 94 may be formed integrally.

According to this modification, the filler having flowed through the introduction hole 90 is introduced into the rear-end-side expansion section 36 of the spacer body 24, whereas the filler having flowed through the introduction hole 88 and the communication passage 92 is introduced to substantially the center of the spacer body 24 in the axial direction, and the filler having flowed through the introduction hole 86 and the bypass passage 94 is introduced into the distal-end-side expansion section 38 of the spacer body 24. Therefore, in the case where the spacer 18h according to this modification is used, also, the same effects as those obtained in the above-described embodiment can be obtained.

(Ninth Modification)

Next, a spacer 18i according to a ninth modification of the present invention will be described below with reference to FIG. 19A. As shown in FIG. 19A, the spacer 18i according to this modification is provided with a bypass passage 96 in place of the above-described bypass passage 28.

Like the bypass passage 42 according to the first modification, the bypass passage 96 has a distal end portion secured to a distal end portion of the spacer body 24. Therefore, according to this modification, the same effects as those of the spacer 18a according to the first modification can be obtained.

Further, the bypass passage 96 is formed with a plurality of small holes (outlets) 98 in a distal end portion thereof. This ensures that a filler having flowed through the bypass passage 96 can be reliably made to flow out into a distal end portion of the spacer body 24 through the small holes 98.

(Tenth Modification)

Next, a spacer 18j according to a tenth modification of the present invention will be described below with reference to FIG. 19B. As shown in FIG. 19B, the spacer 18j according to this modification is provided with a plurality of bypass passages 100 in place of the above-described bypass passage 28.

The plurality of bypass passages 100 extend radially in the inside of the spacer body 24, in the state of being fixed to a rear end portion of the introduction section 26 by a fixing member 102. Besides, in this modification, the sum of the flow path cross-sectional areas of these bypass passages 100 is the same as the flow path cross-sectional area S1 of the above-described bypass passage 28.

According to this modification, the plurality of bypass passages 100 extend radially inside the spacer body 24, so that the distal-end-side expansion section 38 of the spacer body 24 can be expanded substantially uniformly in the circumferential direction.

While the present invention has been described above by showing the preferred embodiment and modifications thereof, the invention is not to be restricted to the embodiment and modifications, and, naturally, various alterations are possible within the scope of the gist of the invention.

For instance, as the spacer of the expanding device according to the present invention, there may be used a spacer which is obtained by arbitrarily combining features of the spacers 18a to 18j of the above-described first to tenth modifications of the present invention.

What is claimed is:

1. A spacer configured to be set indwelling between bones and to expand a spacing between the bones, the spacer comprising:

a spacer body configured to be expandable, the spacer body including a first space inside a rear-end-side expansion section of the spacer body and a second space inside a distal-end-side expansion section of the spacer body, the first and second spaces being in fluid communication with each other;

an introduction section through which a filler passes to be introduced into the first space inside the rear-end-side expansion section of the spacer body; and a bypass passage through which part of the filler in the introduction section is introduced into the second space inside the distal-end-side expansion section of the spacer body.

2. The spacer according to claim 1, wherein the introduction section and the bypass passage are so formed that the introduction of the filler into the rear-end-side expansion section through the introduction section and the introduction of the filler into the distal-end-side expansion section through the bypass passage are started substantially simultaneously, and that the quantity of the filler introduced into the rear-end-side expansion section through the introduction section per unit time and the quantity of the filler introduced into the distal-end-side expansion section through the bypass passage per unit time are substantially the same.

3. The spacer according to claim 1,
wherein the introduction section is connected to a rear end portion of the spacer body, and an outlet for the filler of the bypass passage is located at a distal end portion of the spacer body.

4. The spacer according to claim 1,
wherein the bypass passage is disposed inside the spacer body.

5. The spacer according to claim 4,
wherein the bypass passage is fixed to an inner surface of the spacer body.

6. The spacer according to claim 5,
wherein the bypass passage is fixed to at least one of a distal end portion and a rear end portion of the spacer body.

7. The spacer according to claim 5,
wherein the bypass passage is flexible, and a portion of the bypass passage that is located inside the spacer body is secured to an inner surface of the spacer body over substantially the whole length of the portion.

8. The spacer according to claim 4,
wherein the introduction section extends to the rear-end-side expansion section in the spacer body, and
an outlet for the filler of the bypass passage is located at the distal-end-side expansion section.

9. The spacer according to claim 1,
wherein the bypass passage is flexible, and is fixed to an outer surface of the spacer body in a state of being disposed outside of the spacer body.

10. The spacer according to claim 1, wherein a flow path cross-section area of the bypass passage is substantially the same as a flow path cross-sectional area on an outside of the bypass passage at a rear end portion of the spacer body.

11. The spacer according to claim 1, wherein an introduction hole of the introduction section communicates with the first space inside the rear-end-side expansion section, and the bypass passage communicates with the introduction hole.

12. An expanding device configured to expand a spacing between bones, comprising:
a spacer configured to be disposed between the bones and to be expanded when disposed between the bones, the spacer including a first space inside a rear-end-side expansion section of the spacer and a second space inside a distal-end-side expansion section of the spacer, the first and second spaces being in fluid communication with each other;
a catheter possessing a distal end at which is located the spacer and configured to introduce a filler into the spacer; and
a sheath having a lumen through which the catheter is inserted and configured to house the spacer before expansion,
wherein the spacer includes:
a spacer body configured to be expandable;
an introduction section through which the filler is introduced into the first space inside the rear-end-side expansion section of the spacer body; and
a bypass passage through which part of the filler in the introduction section is introduced into the second space inside the distal-end-side expansion section of the spacer body.

* * * * *